(12) United States Patent
Zhou

(10) Patent No.: US 10,610,636 B2
(45) Date of Patent: Apr. 7, 2020

(54) MULTI-DIRECTIONAL INTELLIGENT ENEMA MACHINE

(71) Applicant: SUZHOU GLOBALPEAK HIGH-TECH CO., LTD., Suzhou, Jiangsu (CN)

(72) Inventor: Feng Zhou, Jiangsu (CN)

(73) Assignee: SUZHOU GLOBALPEAK HIGH-TECH CO., LTD. (CN)

( * ) Notice: Subject to any disclaimer, the term of this patent is extended or adjusted under 35 U.S.C. 154(b) by 308 days.

(21) Appl. No.: 15/742,304

(22) PCT Filed: May 31, 2016

(86) PCT No.: PCT/CN2016/084011
§ 371 (c)(1),
(2) Date: Jan. 5, 2018

(87) PCT Pub. No.: WO2017/016306
PCT Pub. Date: Feb. 2, 2017

(65) Prior Publication Data
US 2018/0193551 A1    Jul. 12, 2018

(30) Foreign Application Priority Data

Jul. 28, 2015 (CN) .................... 2015 2 0553959 U

(51) Int. Cl.
*A61M 3/02* (2006.01)
(52) U.S. Cl.
CPC .......... *A61M 3/0254* (2013.01); *A61M 3/025* (2013.01); *A61M 3/0216* (2014.02); *A61M 3/0283* (2013.01); *A61M 2202/0007* (2013.01); *A61M 2205/3331* (2013.01); *A61M 2205/3368* (2013.01); *A61M 2205/36* (2013.01); *A61M 2205/505* (2013.01); *A61M 2210/1064* (2013.01)

(58) Field of Classification Search
CPC .. A61M 3/0216; A61M 3/0254; A61M 3/025; A61M 3/0283; A61M 1/0058; A61M 1/006; A61M 1/0064
USPC .................................................. 604/27, 19
See application file for complete search history.

(56) References Cited

U.S. PATENT DOCUMENTS 3,757,806 A * 9/1973 Bhaskar ............... A61C 17/028
134/191
5,439,022 A * 8/1995 Summers ............ A61M 1/0062
137/102

(Continued)

*Primary Examiner* — Bhisma Mehta
*Assistant Examiner* — Nidah M Hussain

(57) ABSTRACT

The present invention discloses a multi-directional intelligent enema machine, which comprises a first air pump, a first reversing valve, a medicine feeding unit, a first check valve, a heating unit and a first insertion tube which are sequentially connected, and further comprises a first flushing unit, a second flushing unit, a second air pump, an air intake unit, a waste discharge unit and a circuit control unit. The units are connected by a pipeline and controlled and monitored by the circuit control unit. The enema machine of the present invention is safe, reliable, efficient and convenient, and has the functions of liquid infusing, flushing, waste discharging and mixing the intake air and liquid, and can monitor the pressure, temperature and liquid level and so on at the same time.

20 Claims, 11 Drawing Sheets

(56) References Cited

U.S. PATENT DOCUMENTS

2005/0148954 A1* 7/2005 Abell .................... A61M 3/022
  604/276
2014/0236074 A1* 8/2014 Faif .................... A61M 13/003
  604/26
2016/0206805 A1* 7/2016 Hassidov ............ A61M 1/0031

* cited by examiner

MULTI-DIRECTIONAL INTELLIGENT ENEMA MACHINE

FIELD

The present invention relates to the technical field of medical devices, and in particular to a multi-directional intelligent enema machine.

BACKGROUND

Enema method refers to that a catheter is inserted into the colon from the anus through the rectum to infuse fluid to achieve laxative exhaust treatment, which can stimulate peristalsis, soften and clear excrement, cool, expedite, and dilute the intestinal toxic, and reduce intestinal toxic absorption. Therefore, it has good clinical application prospects, especially enema before an intestinal surgery, which can not only realize thorough cleaning, provide a cleaner surgical area, reduce the risk of incision contamination; but can also be conducive to postoperative recovery of intestinal functions, and reduce postoperative abdominal distension and defecation pain. The prior art enema machine has the following defects: (1) when the medicinal solution is injected into the human body through the pipeline of the medicinal feeding unit, the residual medicinal solution in the pipeline of the medicinal feeding unit cannot be removed and the infection easily occurs; (2) during enema treatment, if the pressure in the medicine feeding and liquid outlet pipelines cannot be effectively monitored, it is extremely easy to trigger a medical accident; (3) if the liquid medicine infused into the human body is not heated and preserved to the appropriate temperature of the human body, it can easily cause the human body discomfort; and (4) when the insertion tube is divided into the waste tube and the medicine feeding tube for two-way use, the operation is cumbersome, and when used as the same way, it may easily cause cross-infection.

SUMMARY

In view of the shortcomings existing in the prior art, an object of the present invention is to provide a multi-directional intelligent sausage enema machine which is safe, reliable, efficient and convenient and has the functions of liquid infusing, flushing, waste discharging and mixing the intake air and liquid, and can monitor pressure, temperature and level and the like at the same time.

In order to achieve the above object, the technical solution adopted by the present invention is as follows:

a multi-directional intelligent enema machine, comprising a first air pump, a first reversing valve, a medicine feeding unit, a first check valve, a heating unit and a first insertion tube which are sequentially connected, wherein a first three-way connector is arranged between the medicine feeding unit and the first check valve;

further comprising a first flushing unit and a second flushing unit, wherein the first flushing unit and the medicine feeding unit are connected in parallel between as outlet end of the first reversing valve and the first three-way connector; a second three-way connector is arranged between the first check valve and the heating unit, an inlet end of the second flushing unit is connected to the second three-way connector, and a waste liquid bottle connected to an outlet end of the second flushing unit;

further comprising a second air pump and an air intake unit which are sequentially connected, wherein an outlet end of the second air pump is connected to an inlet end of the air intake unit; a third three-way connector is provided between the first check valve and the second three-way connector, and an outlet end of the air intake unit is connected to the third three-way connector;

further comprising a waste discharge unit, wherein the waste discharge unit comprises a waste discharge check valve and a third reversing valve, an inlet end of the waste discharge check valve is connected to a second insertion tube, an outlet end of the waste discharge check valve is connected to an inlet end of the waste liquid bottle, and the second insertion tube is connected to the first insertion tube to form a total insertion tube; an inlet end of the third reversing valve is connected to an outlet end of the waste liquid bottle, and an outlet end of the third reversing valve is connected to the inlet end of the second air pump; and further comprising a circuit control unit, wherein the circuit control unit comprises a main control circuit and a power supply circuit, an air pump circuit, a valve circuit, a heating circuit, an LCD touch screen, a key control circuit and a foot switch circuit which are connected to the main control circuit, and the power supply circuit is also connected to the air pump circuit, the valve circuit, the heating circuit, the LCD touch screen, the foot switch circuit.

As a preferred solution, the heating unit comprises a first heating pinch valve and a heating component which are connected sequentially, an inlet end of the first heating pinch valve is connected to the second three-way connector, and an outlet end of the heating component is connected to the first insertion tube.

As a preferred solution, the medicine feeding unit comprises a pressure relief valve, a liquid medicine bottle and a medicine feeding check valve which are sequentially connected, an inlet end of the pressure relief valve is connected to the outlet end of the first reversing valve, and an outlet end of the medicine feeding check valve is connected to the first three-way connector.

As a preferred solution, the first flushing unit comprises a first flushing check valve, an inlet end of the first flushing check valve is connected to the outlet end of the first reversing valve, and an outlet end of the first flushing check valve is connected to the first three-way connector.

As a preferred solution, the second flushing unit comprises a flushing pinch valve and a second flushing check valve which are sequentially connected, an inlet end of the flushing pinch valve is connected to the second three-way connector, and an outlet end of the second flushing check valve is connected to the inlet end of the waste liquid bottle.

As a preferred solution, the air intake unit comprises a second reversing valve and an air intake check valve which are sequentially connected, an inlet end of the second reversing valve is connected to the outlet end of the second air pump, and an outlet end of the air intake check valve is connected to the third three-way connector.

As a preferred solution, a fourth three-way connector is provided between the second three-way connector and the first heating pinch valve, and a fifth three-way connector is arranged between the heating component and the first intersection tube; a second heating pinch valve is connected between the fourth three-way connector and the fifth three-way connector, an inlet end of the second heating pinch valve is connected to the fourth three-way connector, and an outlet end of the second heating pinch valve is connected to the fifth three-way connector.

As a preferred solution, a first temperature sensor is arranged on the heating component, a second temperature sensor is arranged on the first insertion tube, and the first temperature sensor and the second temperature sensor are both connected to the main control circuit through a temperature sensor circuit.

As a preferred solution, the inlet end of the liquid medicine bottle is provided with a medicine feeding pressure sensor and the medicine feeding pressure sensor is connected to the main control circuit through a pressure sensor circuit; a liquid level sensor is arranged at the outlet end of the liquid medicine bottle, and the liquid level sensor is connected to the main control circuit through a liquid level sensor circuit.

As a preferred solution, a waste discharge pressure sensor is disposed at the outlet end of the waste liquid bottle, and the waste discharge pressure sensor is connected to the main control circuit through a pressure sensor.

Compared with the prior art, the present invention has the following beneficial effects: the present invention is safe, reliable, efficient and convenient, and has the functions of medicine feeding, flushing, discharging, and mixing the intake air and liquid, and can monitor the temperature, level, and pressure of medicine liquid bottles and waste liquid bottles at the same time.

DETAILED DESCRIPTION

The present invention will be further described with reference to specific embodiments. The following embodiments are only used for more clearly illustrating the technical solutions of the present invention, and are not intended to limit the protection scope of the present invention.

Embodiment

Figure 1:
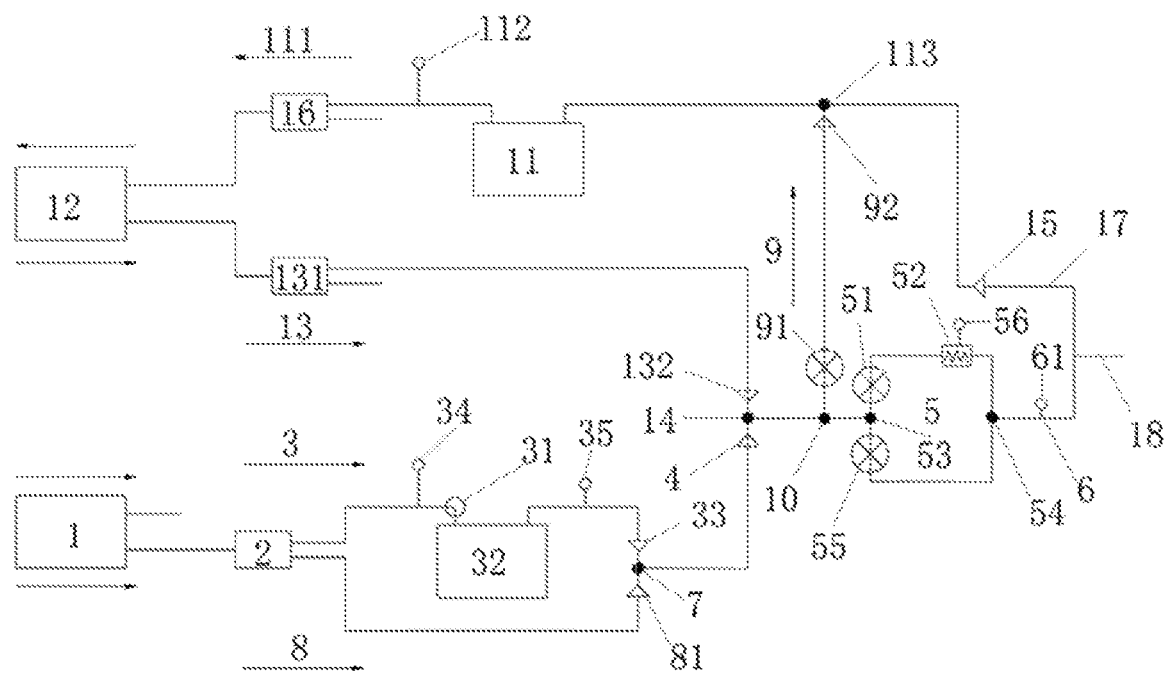
FIG. 1 is a schematic structural view of the present invention.
Figure 2:
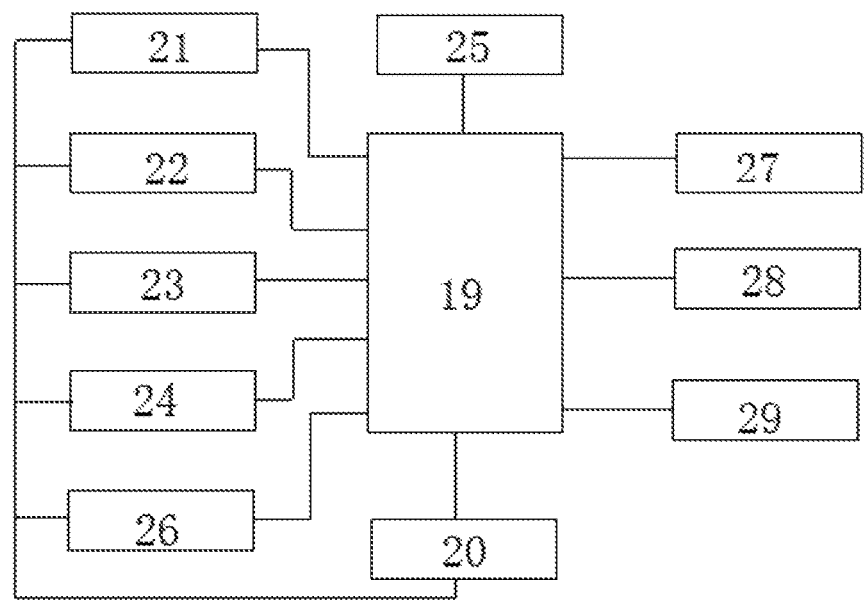
FIG. 2 is a circuit block diagram of a circuit control unit of the present invention.

FIG. 1 shows a multi-directional intelligent enema machine, which comprises a first air pump 1, a first reversing valve 2, a medicine feeding unit 3, a first check valve 4, a heating unit 5 and a first insertion tube 6 which are sequentially connected, wherein a first three-way connector 7 is arranged between the medicine feeding unit 3 and the first check valve 4;

the multi-directional intelligent enema machine further comprises a first flushing unit 8 and a second flushing unit 9, wherein the first flushing unit 8 and the medicine feeding unit 3 are connected in parallel between an outlet end of the first reversing valve 2 and the first three-way connector 7; a second three-way connector 10 is arranged between the first check valve 4 and the heating unit 5, an inlet end of the second flushing unit 9 is connected to the second three-way connector 10, and a waste liquid bottle 11 is connected to an outlet end of the second flushing unit 9;

the multi-directional intelligent enema machine further comprises a second air pump 12 and an air intake unit 13 which are sequentially connected, wherein an outlet end of the second air pump 12 is connected to an inlet end of the air intake unit 13; a third three-way connector 14 is provided between the first check valve 4 and the second three-way connector 10, and an outlet end of the air intake unit 13 is connected to the third three-way connector 14;

the multi-directional intelligent enema machine further comprises a waste discharge unit 111, wherein the waste discharge unit 111 comprises a waste discharge check valve 15 and a third reversing valve 16, an inlet end of the waste discharge check valve 15 is connected to a second insertion tube 17, an outlet end of the waste discharge check valve 15 is connected to an inlet end of the waste liquid bottle 11, and the second insertion tube 17 is connected to the first insertion tube 6 to form a total insertion tube 18; an inlet end of the third reversing valve 16 is connected to an outlet end of the waste liquid bottle 11, and the outlet end of the third reversing valve 16 is connected to the inlet end of the second air pump 12; and as shown in FIG. 2, the multi-directional intelligent enema machine further comprises a circuit control unit, wherein the circuit control unit comprises a main control circuit 19 and a power supply circuit 20, an air pump circuit 21, a valve circuit 22, a heating circuit 23, an LCD touch screen 24, a key control circuit 25 and a foot switch circuit 26 which are both connected to the main control circuit 19, and the power supply circuit 20 is also connected to the air pump circuit 21, the valve circuit 22, the heating circuit 23, the LCD touch screen 24, the foot switch circuit 26.

Preferably, in the present invention, the heating unit 5 comprises a first heating pinch valve 51 and a heating component 52 which are connected sequentially, an inlet end of the first heating pinch valve 51 is connected to the second three-way connector 10, and an outlet end of the heating component 52 connected to the first insertion tube 6. The heating unit 5 is different from the prior art where the heating unit 5 is disposed at the bottom of the liquid medicine bottle 32, avoiding the problem that the liquid medicine in the liquid medicine bottle 32 is heated unevenly, and with the decreasing of the liquid medicine, after the heating unit 5 stops operation, the remaining heat will also rise the temperature of the liquid medicine. The enema machine in the present invention has good temperature persistence and even temperature.

Preferably, in the present invention, the medicine feeding unit 3 comprises a pressure relief valve 31, a liquid medicine bottle 32 and a medicine feeding check valve 33 which are sequentially connected, an inlet end of the pressure relief valve 31 is connected to the outlet end of the first reversing valve 2, and an outlet end of the medicine feeding check valve 33 is connected to the first three-way connector 7. The pressure relief valve 31 is provided such that the enema machine has good safety performance and the pressure between the pipelines is controllable.

Preferably, in the present invention, the first flushing unit 8 comprises a first flushing check valve 81, an inlet end of the first flushing check valve 81 is connected to the outlet end of the first reversing valve 2, and an outlet end of the first flushing check valve 81 is connected to the first three-way connector 7; the second flushing unit 9 comprises a flushing pinch valve 91 and a second flushing check valve 92 which are sequentially connected, an inlet end of the flushing pinch valve 91 is connected to the second three-way connector 10, and an outlet end of the second flushing check valve 92 is connected to the inlet end of the waste liquid bottle 11, such that the enema machine in the present invention has a function of pipeline flushing.

Preferably, in the present invention, the air intake unit 13 comprises a second reversing valve 131 and an air intake check valve 132 which are sequentially connected, an inlet end of the second reversing valve 131 is connected to the outlet end of the second air pump 12, and an outlet end of the air intake check valve 132 is connected to the third three-way connector 14; and the air intake unit 13 is used with the medicine feeding unit 3 jointly, such that the enema machine in the present invention can mix the inflowing liquid and has better effects.

Preferably, in the present invention, a fourth three-way connector 53 is provided between the second three-way connector 10 and the first heating pinch valve 51, and a fifth three-way connector 54 is arranged between the heating component 52 and the first insertion tube 6; a second heating pinch valve 55 is connected between the fourth three-way connector 53 and the fifth three-way connector 54, an inlet end of the second heating pinch valve 55 is connected to the fourth three-way connector 53, and an outlet, end of the second heating pinch valve 55 is connected to the fifth three-way connector 54; the second heating pinch valve 55 is connected in parallel to the heating unit 5, and when the pipeline does not need constant temperature or heating, the second heating pinch valve 55 is opened and the first heating pinch valve 51 is closed, such that the liquid medicine enters the first insertion tube 6 at the second heating pinch valve 55, reducing the pressure load in the pipeline and pushing the liquid medicine to move.

Preferably, in the present invention, a first temperature sensor 56 is arranged on the heating component 52, a second temperature sensor 61 is arranged on the first insertion tube 6, and the first temperature sensor 56 and the second temperature sensor 61 are both connected to the main control circuit 19 through a temperature sensor circuit 27; the first temperature sensor 56 is configured to monitor the heating temperature of the heating component 52, and the second temperature sensor 61 is configured to monitor the temperature of the first insertion tube 6, ensuring that the temperature of the liquid medicine is proper when entering a human body.

Preferably, in the present invention, the inlet end of the liquid medicine bottle 32 is provided with a medicine feeding pressure sensor 34 and the medicine feeding pressure sensor 34 is connected to the main control circuit 19 through a pressure sensor circuit 28; a liquid level sensor 35 is arranged at the outlet end of the liquid medicine bottle 32, and the liquid level sensor 35 is connected to the main control circuit 19 through a liquid level sensor circuit 29; the medicine feeding pressure sensor 34 is configured to monitor the positive pressure and negative pressure of the medicine feeding unit 3, and the liquid level sensor 35 is configured to monitor the liquid medicine level in the liquid medicine bottle 32.

Preferably, in the present invention, a waste discharge pressure sensor 112 is disposed at the outlet end of the waste liquid bottle 11, and the waste discharge pressure sensor 112 is connected to the main control circuit 19 through a pressure sensor 28; and the waste discharge pressure sensor 112 is configured to monitor the positive pressure and negative pressure of the waste discharge unit 111.

During a specific implementation, when used as a medicine feeding function, the first air pump 1 is operated, the first reversing valve 2 is deflated, and the flushing pinch valve 91 is clamped. When the temperature of the first insertion tube 6 is suitable, the first heating pinch valve 51 is clamped, the second heating pinch valve 55 is released, and the liquid medicine enters the human body through the pipeline after flowing out of the liquid medicine bottle 32. When the temperature of the first insertion tube 6 is too low, the first heating pinch valve 52 is released, the second heating pinch valve 55 is clamped, and the liquid medicine enters the human body after flowing out of the liquid medicine bottle 32 and heated by the heating component 52. When used as a flushing function, the first air pump 1 is operated, the first reversing valve 2 is deflated, the flushing pinch valve 91 is released, the first heating pinch valve 51 is clamped, the second heating pinch valve 55 is clamped, and the gas sends the residual liquid medicine to the waste liquid bottle 11 through the first flushing unit 8 and the second flushing unit 9. When used as a waste discharge function, the second air pump 12 is operated, the third reversing valve 16 is sucked off, the flushing pinch valve 91 is clamped, the first heating pinch valve 51 is clamped, the second heating pinch valve 55 is clamped, and the waste liquid in the human body flows from the waste liquid unit 111 to the waste liquid bottle 11 through the second insertion tube 17, here a sixth three-way connector 113 is arranged between the waste discharge check valve 15 and the waste liquid bottle 11, and the sixth three-way connector 113 is connected to an outlet end of the flushing pinch valve 91. In the present invention, three-way connectors are used in many places, making the pipeline structure of the enema machine simple and easy to control. When used as an inflowing liquid mixture function, the first air pump 1 and the second air pump 12 are operated, the first reversing valve 2 and the second reversing valve 131 are deflated, and the flushing pinch valve 91 is clamped. When the temperature of the first insertion tube 6 is suitable, the first heating pinch valve 51 is clamped, the second heating pinch valve 55 is released, and the liquid medicine enters the human body through the pipeline after flowing out of the liquid medicine bottle 32. When the temperature of the first insertion tube 6 is too low, the first heating pinch valve 52 is released, the second heating pinch valve 55 is clamped, and the liquid medicine flows out of the liquid medicine bottle 32 and then enters the human body after being heated by the heating component 52. In the present invention, the first insertion tube 6 and the second insertion tube 17 are connected to form a total insertion tube 18, so the operation is simpler, and liquid discharge and liquid medicine feeding are separated from each other through two ways to avoid cross-infection.

Figure 3:
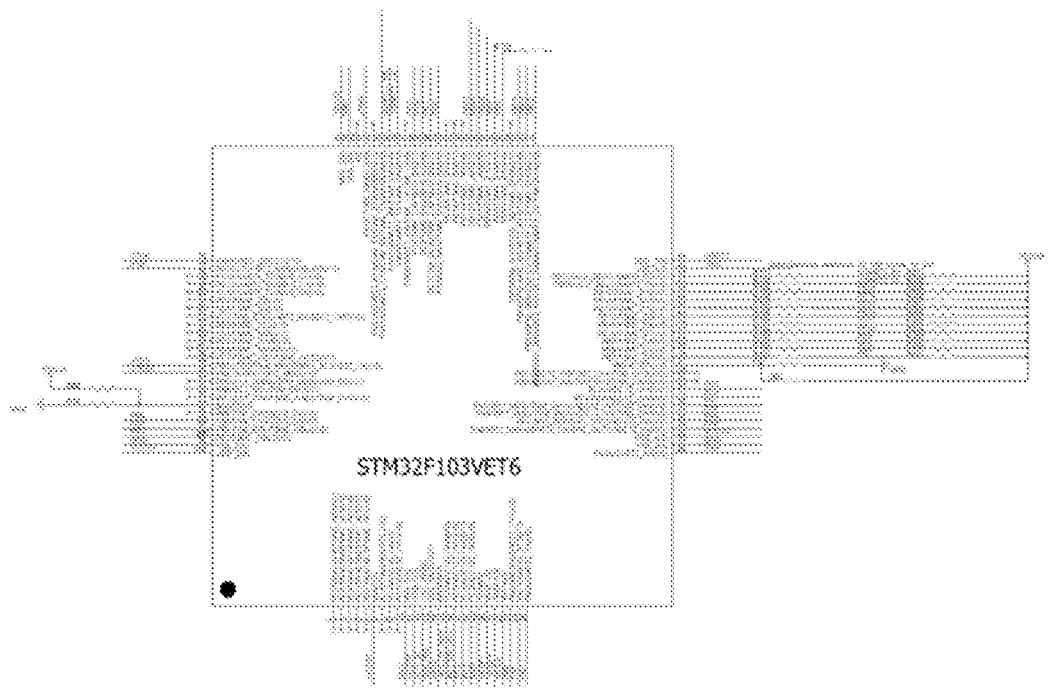
FIG. 3 is a circuit diagram of a main control circuit of the present invention.

FIG. 3 shows a circuit schematic diagram of the main control circuit 19 of the present invention. An STM32F103VE6T micro-controller is adopted to control the operation of each air pump and valve in the pipeline to control the flow directions of liquid, gas and the like and control the operation of the heating component 51 so as to achieve the heating function and stop heating in time when the temperature reaches a predetermined value. Meanwhile, information of the pressure sensor, the temperature sensor, the level sensor and the like is acquired to ensure she normal operation of the machine.

Figure 4:
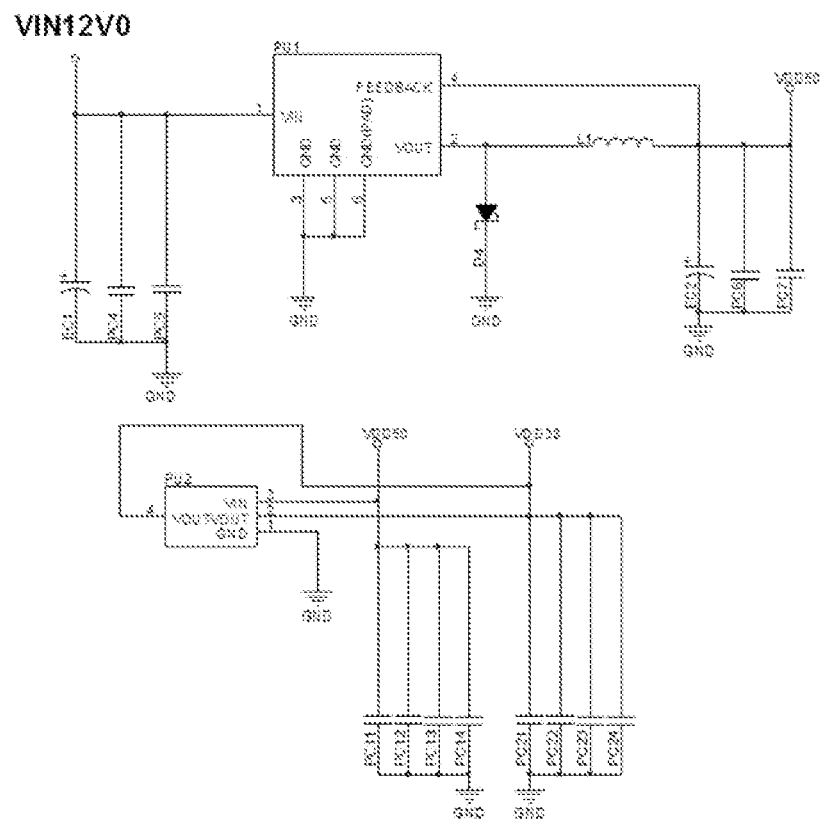
FIG. 4 is a schematic circuit diagram of a power supply circuit of the present invention.

FIG. 4 shows a circuit diagram of the power circuit 20 in the present invention. The power circuit 20 provides power signals required by the main control circuit 19, the air pump circuit 21, the valve circuit 22, the heating circuit 23, the LCD touch screen 24 and the foot switch circuit 26. The grid power 220V is converted into 12V DC via a switch power supply. The 12V DC is converted into a 5V voltage by a DCDC converter chip LM2576S-5.0. The 5V DC is converted into 3.3V by a LDO conversion chip AMS1117-3.3V.

Figure 5:
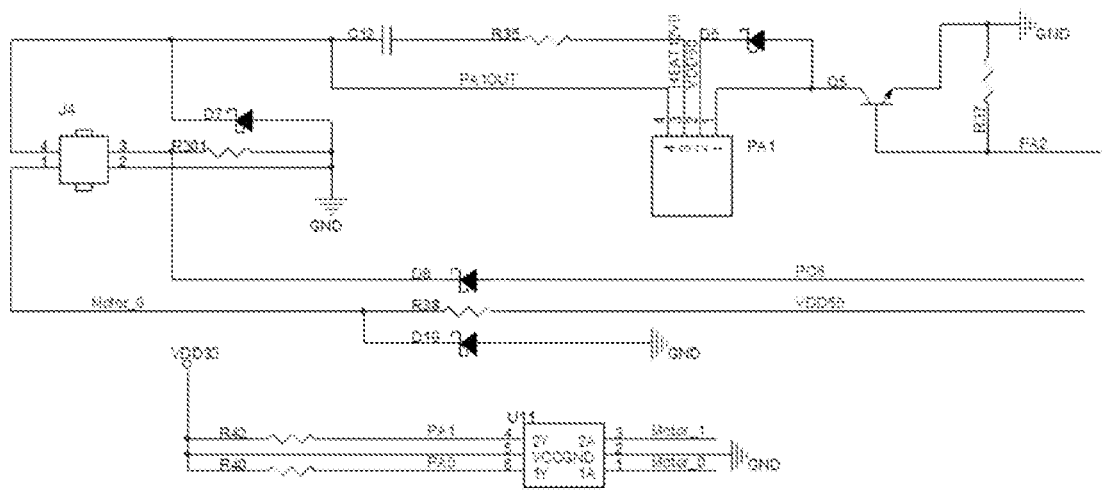
FIG. 5 is a circuit diagram of an air pump circuit of the present invention.

FIG. 5 shows a circuit diagram of the air pump circuit 21 in the present invention which is controlled by a PWM signal of the main control circuit 19, the speed is precisely controlled, and a speed feedback signal is sent back to the main control circuit 19 for real-time adjustment.

Figure 6:
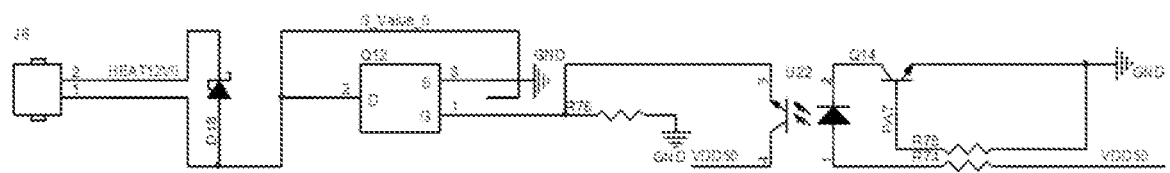
FIG. 6 is a schematic circuit diagram of a valve circuit and a heating circuit of the present invention.

FIG. 6 shows a circuit schematic diagram of the valve circuit 22 and the heating circuit 23 in the present invention. The main control circuit 19 controls each valve and the heating component 52 through switch signals. The control valve determines the flow directions of liquid and gas so as to realize a number of functions of the enema machine. The heating circuit 23 controls the liquid temperature.

Figure 7:
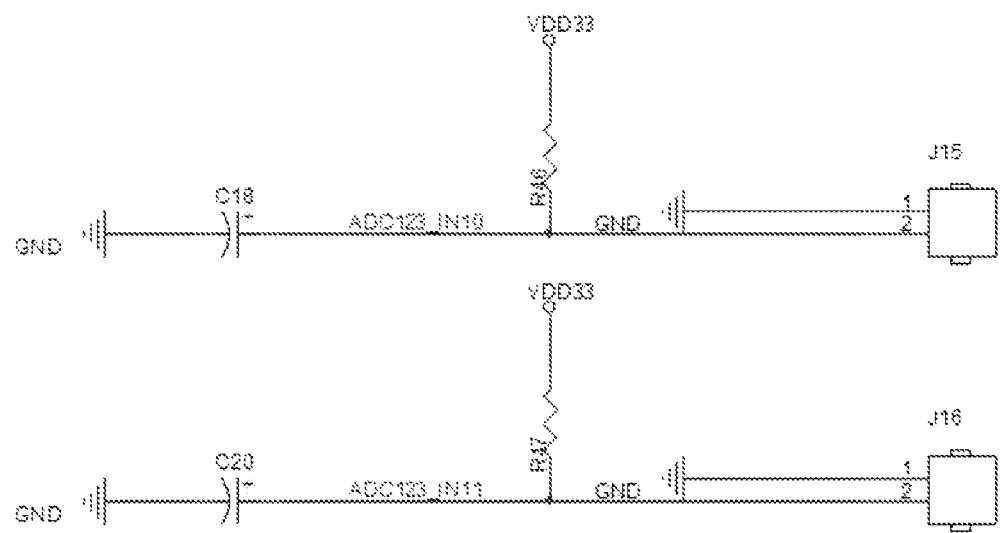
FIG. 7 is a circuit diagram of a temperature sensor circuit of the present invention.

FIG. 7 is a circuit schematic diagram of the temperature sensor circuit 27 in the present invention for obtaining temperature information in the heating component 52 and the first insertion tube 6.

Figure 8:
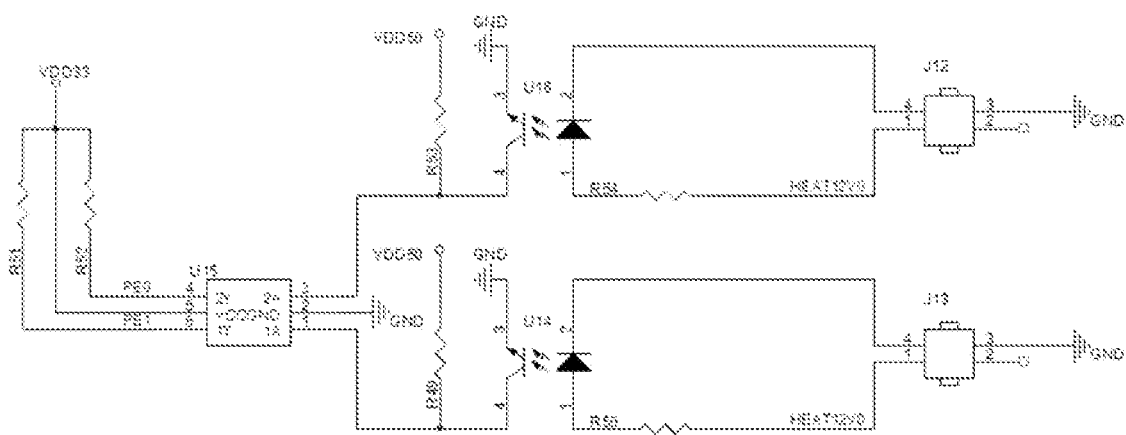
FIG. 8 is a circuit diagram of a liquid level sensor circuit of the present invention.

FIG. 8 is a schematic circuit diagram of the liquid level sensor circuit 29 in the present invention for obtaining liquid level information in the liquid medicine bottle 32.

Figure 9:
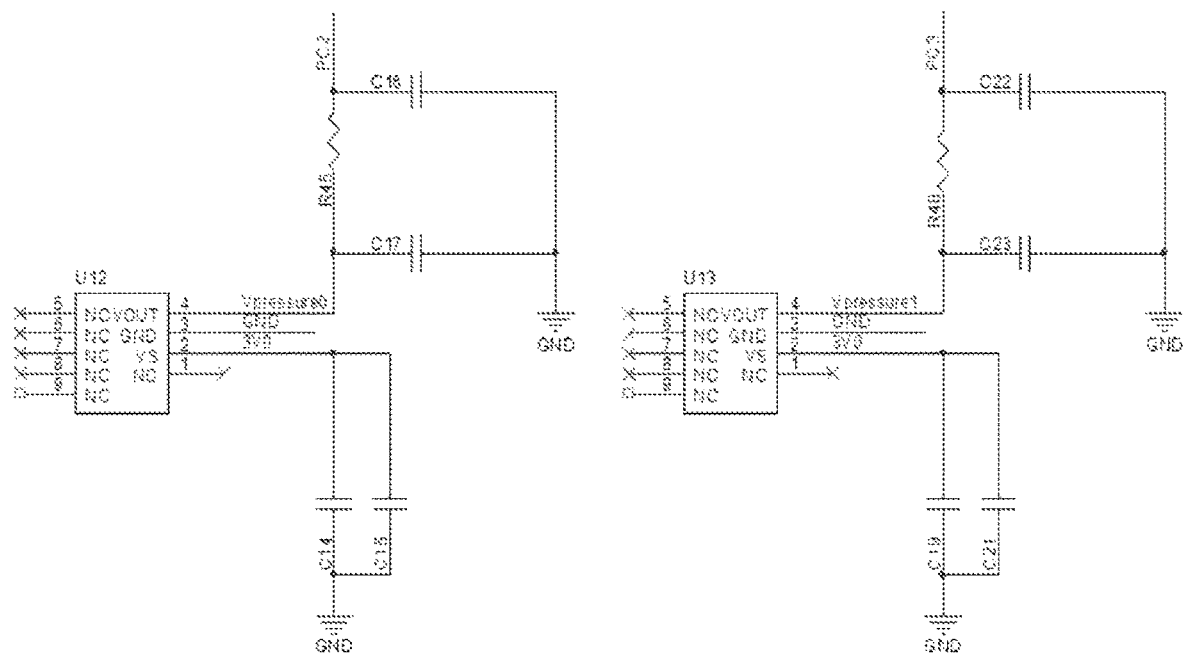
FIG. 9 is a circuit diagram of a pressure sensor circuit of the present invention.

FIG. 9 is a circuit schematic diagram of the pressure sensor circuit 28 in the present invention for obtaining pressure information in the liquid medicine bottle 32 and the waste liquid bottle 11.

Figure 10:
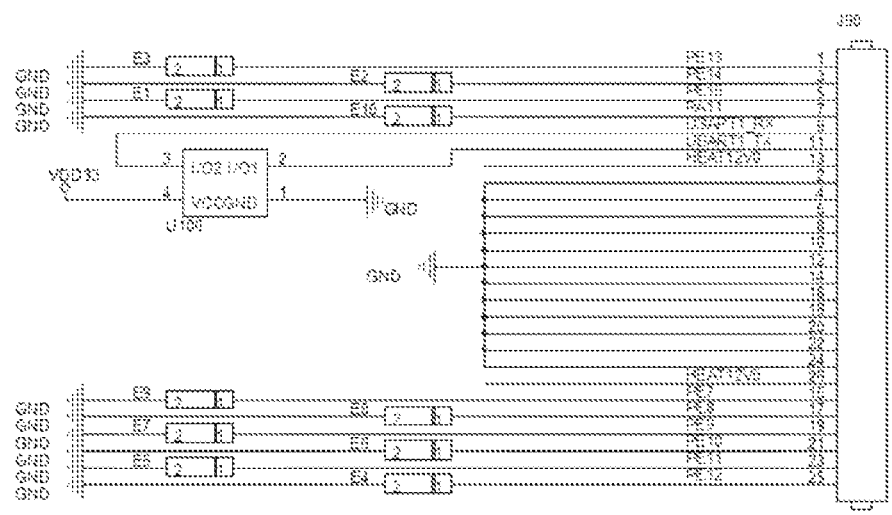
FIG. 10 is a circuit diagram of a LCD touch screen and a key control circuit of the present invention.

FIG. 10 is a circuit diagram of the LCD touch screen 24 and the key control circuit 25 in the present invention. The LCD touch screen circuit 24 is used to display signals and operating parameters of the enema machine. The operating parameters of the enema machine can be adjusted to turn on or off the enema machine. The key control circuit 25 can also adjust the operating parameters of the enema machine, giving a user more choices.

Figure 11:
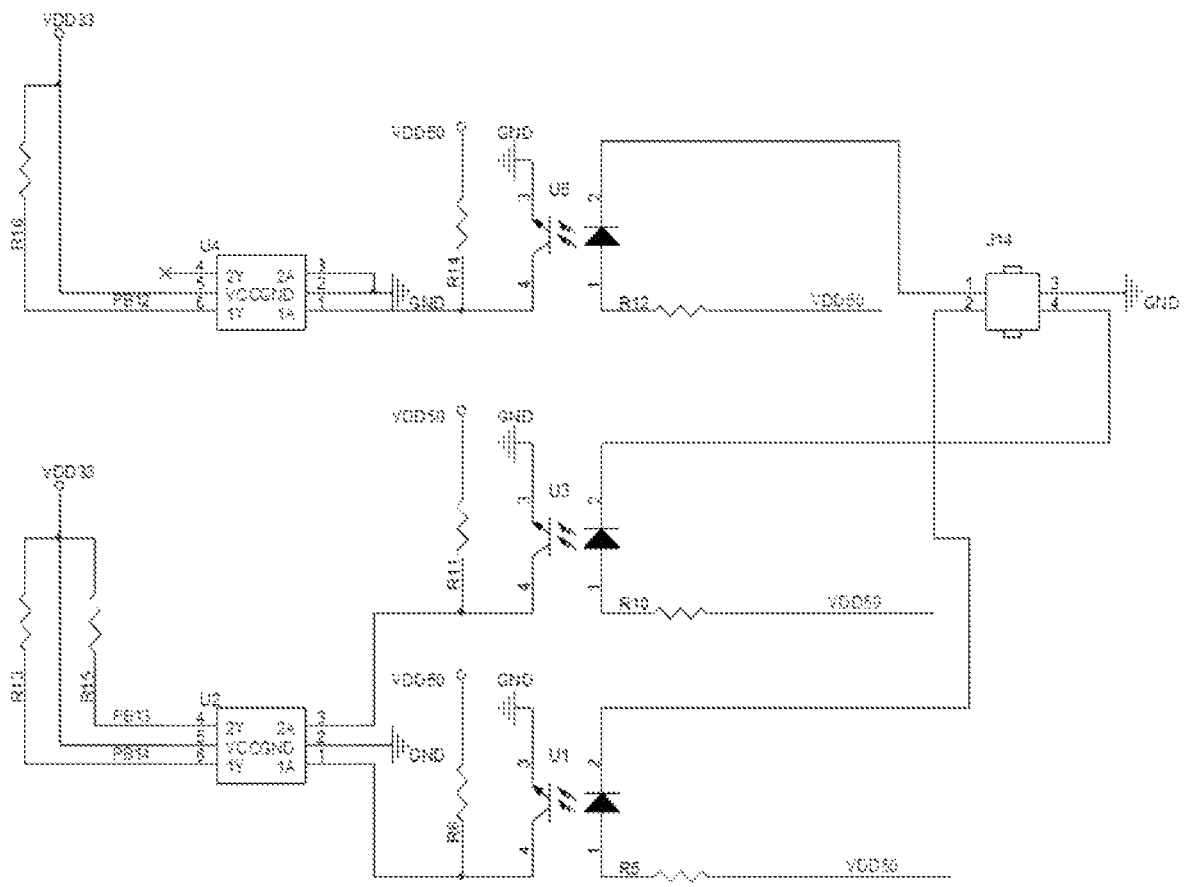
FIG. 11 is a circuit diagram of a foot switch circuit of the present invention.

FIG. 11 shows a circuit diagram of the foot switch circuit 26 in the present invention which provides the function of turning on or off the enema machine by foot.

The above is only the preferred embodiments of the present invention, and it should be noted that those skilled in the art may make some improvements and changes without departing from the technical principles of the present invention Shape, these improvements and deformations should also be regarded as the scope of the present invention.

What is claimed is:

1. A multi-directional intelligent enema machine, comprising
a first air pump, a first reversing valve, a medicine feeding unit, a first check valve, a heating unit and a first insertion tube which are sequentially connected, wherein a first three-way connector is arranged between the medicine feeding unit and the first check valve;
further comprising a first flushing unit, and a second flushing unit, wherein the first flushing unit and the medicine feeding unit are connected in parallel between an outlet end of the first reversing valve and the first three-way connector; a second three-way connector is arranged between the first check valve and the heating unit, an inlet end of the second flushing unit is connected to the second three-way connector, and a waste liquid, bottle is connected to an outlet end of the second flushing unit;
further comprising a second air pump and an air intake unit which are sequentially connected, wherein an outlet end of the second air pump is connected to an inlet end of the air intake unit; a third three-way connector is provided between the first check valve and the second three-way connector, and an outlet end of the air intake unit is connected to the third three-way connector;
further comprising a waste discharge unit, wherein the waste discharge unit comprises a waste discharge check valve and a third reversing valve, an inlet end of the waste discharge check valve is connected to a second insertion tube, an outlet end of the waste discharge check valve is connected to an inlet end of the waste liquid bottle, and the second insertion tube is connected to the first insertion tube to form a total insertion tube; an inlet end of the third reversing valve is connected to an outlet end of the waste liquid bottle, and an outlet end of the third reversing valve is connected to an inlet end of the second air pump; and
further comprising a circuit control unit, wherein the circuit control unit comprises a main control circuit and a power supply circuit, an air pump circuit, a valve circuit, a heating circuit, an LCD touch screen, a key control circuit and a foot switch circuit which are connected to the main control circuit, and the power supply circuit is also connected to the air pump circuit, the valve circuit, the heating circuit, the LCD touch screen and the foot switch circuit.

2. The multi-directional intelligent enema machine according to claim 1, wherein a waste discharge pressure sensor is disposed at the outlet end of the waste liquid bottle, and the waste discharge pressure sensor is connected to the main control circuit through a pressure sensor.

3. The multi-directional intelligent enema machine according to claim 1, wherein the heating unit comprises a first heating pinch valve and a heating component which are connected sequentially, an inlet end of the first heating pinch valve is connected to the second three-way connector, and an outlet end of the heating component is connected to the first insertion tube.

4. The multi-directional intelligent enema machine according to claim 3, wherein a fourth three-way connector is provided between the second three-way connector and the first heating pinch valve, and a fifth three-way connector is arranged between the heating component and the first insertion tube; a second heating pinch valve is connected between the fourth three-way connector and the fifth three-way connector, an inlet end of the second heating pinch valve is connected to the fourth three-way connector, and an outlet end of the second heating pinch valve is connected to the fifth three-way connector.

5. The multi-directional intelligent enema machine according to claim 3, wherein a first temperature sensor is arranged on the heating component, a second temperature sensor is arranged on the first insertion tube, and the first temperature sensor and the second temperature sensor are both connected to the main control circuit through a temperature sensor circuit.

6. The multi-directional intelligent enema machine according to claim 3, wherein the medicine feeding unit comprises a pressure relief valve, a liquid medicine bottle and a medicine feeding check valve which are sequentially connected, an inlet end of the pressure relief valve is connected to the outlet end of the first reversing valve, and an outlet end of the medicine feeding check valve is connected to the first three-way connector.

7. The multi-directional intelligent enema machine according to claim 6, wherein an inlet end of the liquid medicine bottle is provided with a medicine feeding pressure sensor and the medicine feeding pressure sensor is connected to the main control circuit through a pressure sensor circuit; a liquid level sensor is arranged at an outlet end of the liquid medicine bottle, and the liquid level sensor is connected to the main control circuit through a liquid level sensor circuit.

8. The multi-directional intelligent enema machine according to claim 6, wherein a fourth three-way connector is provided between the second three-way connector and the first heating pinch valve, and a fifth three-way connector is arranged between the heating component and the first insertion tube; a second heating pinch valve is connected between the fourth three-way connector and the fifth three-way connector, an inlet end of the second heating pinch valve is connected to the fourth three-way connector, and an outlet end of the second heating pinch valve is connected to the fifth three-way connector.

9. The multi-directional intelligent enema machine according to claim 6, wherein a first temperature sensor is arranged on the heating component, a second temperature sensor is arranged on the first insertion tube, and the first temperature sensor and the second temperature sensor are both connected to the main control circuit through a temperature sensor circuit.

10. The multi-directional intelligent enema machine according to claim 6, wherein the first flushing unit comprises a first flushing check valve, an inlet end of the first flushing check valve is connected to the outlet end of the first reversing valve, and an outlet end of the first flushing check valve is connected to the first three-way connector.

11. The multi-directional intelligent enema machine according to claim 10, wherein a fourth three-way connector is provided between the second three-way connector and the first heating pinch valve, and a fifth three-way connector is arranged between the heating component and the first insertion tube; a second heating pinch valve is connected between the fourth three-way connector and the fifth three-way connector, an inlet end of the second heating pinch valve is connected to the fourth three-way connector, and an outlet end of the second heating pinch valve is connected to the fifth three-way connector.

12. The multi-directional intelligent enema machine according to claim 10, wherein a first temperature sensor is arranged on the heating component, a second temperature, sensor is arranged on the first insertion tube, and the first temperature sensor and the second temperature sensor are both connected to the main control circuit through a temperature sensor circuit.

13. The multi-directional intelligent enema machine according to claim 10, wherein the second flushing unit comprises a flushing pinch valve and a second flushing check valve which are sequentially connected, an inlet end of the flushing pinch valve is connected to the second three-way connector, and an outlet end of the second flushing check valve is connected to the inlet end of the waste liquid bottle.

14. The multi-directional intelligent enema machine according to claim 13, wherein a fourth three-way connector is provided between the second three-way connector and the first heating pinch valve, and a fifth three-way connector is arranged between the heating component and the first insertion tube; a second heating pinch valve is connected between the fourth three-way connector and the fifth three-way connector, an inlet end of the second heating pinch valve is connected to the fourth three-way connector, and an outlet end of the second heating pinch valve is connected to the fifth three-way connector.

15. The multi-directional intelligent enema machine according to claim 13, wherein a first temperature sensor is arranged on the heating component, a second temperature sensor is arranged on the first insertion tube, and the first temperature sensor and the second temperature sensor are both connected to the main control circuit through a temperature sensor circuit.

16. The multi-directional intelligent enema machine according to claim 13, wherein the air intake unit comprises a second reversing valve and an air intake check valve which are sequentially connected, an inlet end of the second reversing valve is connected to the outlet end of the second air pump, and an outlet end of the air intake check valve is connected to the third three-way connector.

17. The multi-directional intelligent enema machine according to claim 16, wherein a fourth three-way connector is provided between the second three-way connector and the first heating pinch valve, and a fifth three-way connector is arranged between the heating component and the first insertion tube; a second heating pinch valve is connected between the fourth three-way connector and the fifth three-way connector, an inlet end of the second heating pinch valve is connected to the fourth three-way connector, and an outlet end of the second heating pinch valve is connected to the fifth three-way connector.

18. The multi-directional intelligent enema machine according to claim 16, wherein a first temperature sensor is arranged on the heating component, a second temperature sensor is arranged on the first insertion tube, and the first temperature sensor and the second temperature sensor are both connected to the main control circuit through a temperature sensor circuit.

19. The multi-directional intelligent enema machine according to claim 16, wherein an inlet end of the liquid medicine bottle is provided with a medicine feeding, pressure sensor and the medicine feeding pressure sensor is connected to the main control circuit through a pressure sensor circuit; a liquid level sensor is arranged at an outlet end of the liquid medicine bottle, and the liquid level sensor is connected to the main control circuit through a liquid level sensor circuit.

20. The multi-directional intelligent enema machine according to claim 16, wherein a waste discharge pressure sensor is disposed at the outlet end of the waste liquid bottle, and the waste discharge pressure sensor is connected to the main control circuit through a pressure sensor.

* * * * *